(12) United States Patent
Watanabe et al.

(10) Patent No.: US 7,872,164 B2
(45) Date of Patent: Jan. 18, 2011

(54) PROCESS FOR PRODUCING 4,9-DIBROMODIAMANTANE

(75) Inventors: Katsuyuki Watanabe, Haibara-gun (JP); Kensuke Morita, Haibara-gun (JP); Masaya Nakayama, Odawara (JP)

(73) Assignee: Fujifilm Corporation, Tokyo (JP)

( * ) Notice: Subject to any disclaimer, the term of this patent is extended or adjusted under 35 U.S.C. 154(b) by 128 days.

(21) Appl. No.: 12/440,672

(22) PCT Filed: Sep. 25, 2007

(86) PCT No.: PCT/JP2007/069149

§ 371 (c)(1),
(2), (4) Date: Mar. 10, 2009

(87) PCT Pub. No.: WO2008/047588

PCT Pub. Date: Apr. 24, 2008

(65) Prior Publication Data

US 2010/0048962 A1 Feb. 25, 2010

(30) Foreign Application Priority Data

Sep. 25, 2006 (JP) ............................. 2006-258946

(51) Int. Cl.
*C07C 17/093* (2006.01)
(52) U.S. Cl. ...................................... 570/254; 570/252
(58) Field of Classification Search ................. 570/252, 570/254

See application file for complete search history.

(56) References Cited

U.S. PATENT DOCUMENTS

2005/0276964 A1 12/2005 Watanabe et al.

OTHER PUBLICATIONS

Matthew C. Davis, selective apical bromination of diamantane and conversion to the dihydroxy and dicarboxylic acid derivatives, Synthetic Communication, 36, 3509-3515, 2006.*
T.M. Gund et al: "The Functionalization of Diamantane". Tetrahedron Lett., No. 56, 1970, pp. 4875-4878, XP002467813.
T.M.Gund: "The ionic bromination of diamantane", Tetrahedron Lett., No. 19, 1971, pp. 1583-1586, XP002467814.
T.M.Gund: "Diamantane. III Preparation and solvolysis of diamantyl bromides", J.Org.Chem., vol. 39, No. 20, 1974, pp. 2995-3003, XP002467815.
T. M. Gund et al."Diamantane.II. Preparation of derivatives of diamantane", Journal of Organic Chemistry, vol. 39 No. 20, 1974 pp. 2987-2994.

* cited by examiner

Primary Examiner—Jafar Parsa
(74) Attorney, Agent, or Firm—Sughrue Mion, PLLC

(57) ABSTRACT

A process for selectively producing 4,9-dibromodiamantane includes a step of reacting diamantane with bromine in the presence of a Lewis acid and a solvent, wherein the solvent comprises a substituted or unsubstituted, straight-chain, branched-chain or cyclic saturated hydrocarbon containing from 3 to 10 carbon atoms, and a reaction solution after the step satisfies Formula (1):

$$A/(A+B+C+D+E) > 0.80 \quad \text{Formula (1)}$$

wherein A represents an area ratio (%) of 4,9-dibromodiamantane obtained by gas chromatography of the reaction solution, B represents an area ratio of diamantane, C represents a sum of an area ratio of 1-bromodiamantane and an area ratio of 4-bromodiamantane, D represents an area ratio of tribromodiamantane, and E represents a sum of an area ratio of 1,6-dibromodiamantane and an area ratio of 1,4-dibromodiamantane.

4 Claims, No Drawings

PROCESS FOR PRODUCING 4,9-DIBROMODIAMANTANE

TECHNICAL FIELD

The present invention relates to a process for producing 4,9-dibromodiamantane and, more particularly, to a process for producing industrially useful 4,9-dibromodiamantane in high yield with producing a less amount of by-products.

BACKGROUND ART

Diamantane derivatives have found various useful applications. For example, in the field of electronic materials, with the progress of high integration, multifunction and high performance, circuit resistance and condenser capacity between wirings have been increased thus causing increase of electric power consumption and delay time. Reduction of parasitic resistance and parasitic capacity are in demand for the purpose of attaining acceleration of devices by reducing this delay time. As one of the concrete measures for reducing this parasitic capacity, an attempt has been made to cover periphery of wiring with a low dielectric interlayer insulating film. Also, the interlayer insulating film is required to have superior heat resistance which is enough to withstand the thin film formation step at the time of producing mounting substrates. Since diamantane has a small electronic polarization and has a rigid, diamond-like saturated hydrocarbon structure, it is known to be useful as a constituent of an interlayer insulating film having low dielectric constant and high heat resistance. As one example thereof, reference may be made to US Patent Application Publication No. 2005/276964.

In synthesizing useful diamantane derivatives having various functional groups, brominated diamantanes play an important role as intermediates for synthesis of the derivatives. That is, a bromine atom on diamantane can be converted to a OH group, an amino group, a SH group, a carboxyl group, a formyl group, an acyl group, an amido group, an ethynyl group, an alkyl group, an aryl group or the like.

Regarding processes for synthesizing bromine-substituted diamantanes, there have been made several reports. For example, as is described in Journal of Organic Chemistry, 39, 2987-3003 (1974), a process of synthesizing a mono-bromodiamantane, a dibromodiamantane, a tribromodiamantane and a tetrabromodiamantane by acting bromine in the presence of a catalytic amount of aluminum bromide has been disclosed. Of these, the dibromodiamantane is known to include three isomers of 1,4-dibromodiamantane, 4,9-dibromodiamantane and 1,6-dibromodiamantane. It has been difficult to selectively synthesize 4,9-dibromodiamantane alone in high yield among them, and no effective processes have been known. An attempt to synthesize 4,9-dibromodiamantane under conventionally known conditions results in simultaneous production of other dibromodiamantane isomers and monobromodiamantanes and tribromodiamantanes as well as 4,9-dibromodiamantane. Purification of such product by repeating recrystallization or column chromatography results in a serious reduction of yield, and the purified product has only insufficient purity. Also, in the above-described process, generation of heat in the bromination reaction is so large that it is difficult to control the inside temperature, thus scale-up of the reaction being difficult. In addition, bumping of bromine might threaten safety of workers. Thus, in view of these points and industrial productivity, it has been demanded to largely improve the process.

DISCLOSURE OF THE INVENTION

In consideration of these problems with the conventional art, the invention provides a process which can selectively produce 4,9-dibromodiamantane in high yield.

As a result of intensive investigations, the inventors have found that the above-described problems can be solved by selectively producing 4,9-dibromodiamantane in high yield according to the following process, thus having achieved the invention.

<1> A process for selectively producing 4,9-dibromodiamantane, comprising:

a step of reacting diamantane with bromine in the presence of a Lewis acid and a solvent, wherein the solvent comprises a substituted or unsubstituted straight-chain saturated hydrocarbon containing from 3 to 10 carbon atoms, a substituted or unsubstituted branched-chain saturated hydrocarbon containing from 3 to 10 carbon atoms, or a substituted or unsubstituted cyclic saturated hydrocarbon containing from 3 to 10 carbon atoms, and a reaction solution after the step satisfies Formula (1):

$$A/(A+B+C+D+E) > 0.80 \quad \text{Formula (1)}$$

wherein A represents an area ratio (%) of 4,9-dibromodiamantane obtained by gas chromatography of the reaction solution, B represents an area ratio of diamantane, C represents a sum of an area ratio of 1-bromodiamantane and an area ratio of 4-bromodiamantane, D represents an area ratio of tribromodiamantane, and E represents a sum of an area ratio of 1,6-dibromodiamantane and an area ratio of 1,4-dibromodiamantane.

<2> The process as described in <1>, wherein the bromine ($Br_2$) is in an amount of from 3.5 to 7.0 mol per 1 mol of the diamantane.

<3> The process as described in <1>, wherein the solvent is selected from the group consisting of n-hexane, cyclohexane and n-heptane.

<4> The process as described in <1>, wherein the solvent is in an amount of from 3 to 7 ml per 1 g of the diamantane.

BEST MODE FOR CARRYING OUT THE INVENTION

The invention will be described in detail below.

Diamantane to be used in the invention may be a commercially available product, or can easily be synthesized according to processes described in literatures (e.g., Organic Synthetis, Vol. 53, p. 70).

As the Lewis acid which can be used in the invention, any Lewis acid may be employed that does not exert detrimental effects on progress of the reaction. However, aluminum chloride, aluminum bromide, iron chloride and iron bromide are preferred, with aluminum bromide being particularly preferred. The amount of Lewis acid to be used varies depending upon reaction conditions (kind of Lewis acid, concentration, temperature, kind of solvent, amount of bromine, etc.), but is preferably from 0.01 to 0.5 mol, more preferably from 0.03 to 0.3 mol, particularly preferably from 0.05 to 0.25 mol, per mol of diamantane.

As the reaction solvent which can be used in the invention, substituted or unsubstituted, straight, branched or cyclic saturated hydrocarbons containing from 3 to 10 carbon atoms (e.g., 1-chloropropane, 1-nitropropane, 1-bromobutane, n-pentane, cyclopentane, n-hexane, cyclohexane, 1-methyl-cyclohexane, n-heptane, n-octane, n-nonane and n-decane) are preferred, unsubstituted, straight or cyclic saturated hydrocarbons containing from 5 to 8 carbon atoms are more preferred, and n-hexane, cyclohexane and n-heptane are particularly preferred.

Examples of substituents which saturated hydrocarbons to be used in the invention as reaction solvents may have include a halogen atom and a nitro group. The saturated hydrocarbons having such substituents have a molecular weight of preferably 120 or less.

It has been found that use of the saturated hydrocarbon solvent serves to unexpectedly largely improve selectivity of the reaction and yield and that the amount of heat generated upon bromination is unexpectedly small, thus the end product being produced safely on a large scale with good productivity.

The amount of the reaction solvent is preferably from 1 to 20 ml, more preferably from 2 to 20 ml, particularly preferably from 3 to 7 ml, per g of diamantane.

The amount of bromine (as $Br_2$) to be used in the invention is preferably from 2.0 to 10 mol, more preferably from 2.5 to 8.0 mol, particularly preferably from 3.5 to 7.0 mol, per mol of diamantane.

It is not particularly limited when to add bromine but, in view of enhancing selectivity of bromination, it is particularly preferred to dropwise add bromine in the presence of diamantane, Lewis acid and a reaction solvent with keeping the inside temperature of the reaction vessel at 0° C. or lower. Bromine can be added in a liquid form, i.e., as such or as a solution diluted with a solvent which can dissolve bromine.

The inside temperature upon reaction is preferably from −20° C. to 10° C., more preferably from −15° C. to 5° C., particularly preferably from −10° C. to 0° C. The reaction time is preferably from 10 minutes to 10 hours, more preferably from 1 hour to 8 hours, particularly preferably from 2 hours to 6 hours. It suffices to react for a suitable time by confirming degree of progress of reaction through gas chromatography. In the case where monobromodiamantanes remain, the reaction may be further continued as post-reaction for 1 to 5 hours at 0° C. to 25° C. for the purpose of converting them to the end product.

The reaction is conducted preferably in an atmosphere of an inert gas (e.g., nitrogen or argon).

The reaction products can be identified by gas chromatography of the solution after the reaction. A characteristic feature of the invention is to realize the relation of A/(A+B+C+D+E)>0.80 (wherein A represents an area ratio (%) of 4,9-dibromodiamantane obtained by gas chromatography of the reaction solution, B represents an area ratio of diamantane, C represents a sum of an area ratio of 1-bromodiamantane and an area ratio of 4-bromodiamantane, D represents an area ratio of tribromodiamantane, and E represents a sum of an area ratio of 1,6-dibromodiamantane and an area ratio of 1,4-dibromodiamantane). Here, monobromodiamantane includes 1-substituted diamantane and 4-substituted diamantane, and tribromodiamantane includes 1,4,6-trisubstituted diamantane and 1,4,9-trisubstituted diamantane.

In case when A/(A+B+C+D+E) is equal to or less than 0.80, purification by recrystallization or chromatography becomes difficult, leading to reduction in isolation yield and purity of the end product, which constitutes a problem from the industrial point of view.

A/(A+B+C+D+E) is more preferably equal to or more than 0.90, more preferably equal to or more than 0.95.

Such reaction product can be obtained by the above-mentioned process.

Embodiment

Following Examples serve to illustrate the invention, and are not to be construed to limit the scope thereof A gas chromatography (GC) used in the invention is GC-2010 manufactured by Shimadzu Mfg. Works, with the temperature of the injection inlet being 280° C., the column (DB-5MS; inside diameter: 0.25 mm; 0.25 μm in film thickness× 30 m in length; filler: 5%-Phenyl)-methylpolysiloxane) being manufactured by Agilent Technologies, the column temperature being 180° C. (3 minutes)→10° C./min→280° C. (17 minutes)), and the column flow amount being 0.32 ml/min.

EXAMPLE 1

340 ml of cyclohexane and 25.5 g of aluminum bromide are introduced into a 1000-ml, three-necked flask, followed by stirring the mixture with a mechanical stirrer for 15 minutes at room temperature in an atmosphere of nitrogen. The inside temperature is lowered to 10° C. or lower than that, and 80 g of diamantane is added thereto. Further, the inside temperature is lowered to 3° C., and 12.7 ml of bromine is dropwise added thereto over 5 minutes. Then, the inside temperature is lowered to −5° C., and 115 ml of bromine is dropwise added thereto over 2 hours. During the addition, the inside temperature is kept at −10° C. to −5° C. After completion of the dropwise addition of bromine, the reaction mixture is stirred for further 2 hours with the inside temperature being from −10° C. to −5° C.

At this stage, a sample is obtained from the reaction solution, pre-treated with a hexane/sodium sulfite aqueous solution, and analyzed by gas chromatography (GC). As a result of the analysis, the area ratios of diamantane:monobromodiamantane:4,9-dibromodiamantane:tribromodiamantane:other dibromodiamantanes are found to be 0:7.4:92.6:0:0 (A/(A+B+C+D+E)=0.93). After further stirring for 1 hour at the inside temperature of 25° C., the reaction solution is subjected to analysis by GC, and the area ratios of diamantane:monobromodiamantane:4,9-dibromodiamantane:tribromodiamantane:other dibromodiamantanes are found to be 0:2.9:96.1:1.0:0 (A/(A+B+C+D+E)=0.96).

430 g of sodium sulfite is dissolved in 2000 ml of water and cooled to 10° C. To this aqueous solution is added the reaction solution by portions under stirring. 1200 ml of toluene and 120 g of sodium hydroxide are added thereto, followed by heating to 70° C. The aqueous layer is separated and discarded, and the organic layer is purified twice with each 1000 ml of pure water. Toluene is removed under reduced pressure to concentrate, and 400 ml of acetone is added to the residue, followed by stirring for 1 hour at 10° C. to crystallize. The thus-obtained crystals are filtered to obtain 103 g of 4,9-dibromodiamantane. Yield: 70%. Purity of the powder is found to be 99.0% by GC measurement of the powder.

EXAMPLE 2

4,9-Dibromodiamantane is synthesized in the same manner as in Example 1 except for using 1270 g of diamantane, 5.4 L of cyclohexane, 404 g of aluminum bromide and a total of 2027 ml of bromine. GC measurement of the solution after completion of the reaction reveals that A/(A+B+C+D+E) is 0.93. Yield of 4,9-dibromodiamantane is 1848 g and 79.1 %. Purity of the powder is found to be 99.0% by GC measurement of the powder.

EXAMPLE 3

51 ml of n-heptane, 0.86 g of aluminum bromide and 8.0 g of diamantane are introduced into a 100-ml, four-necked flask, followed by lowering the inside temperature to 3° C. or lower. 11.47 ml of bromine is dropwise added thereto over 2 hours. During the dropwise addition, the inside temperature is kept at −10° C. to −5° C. After completion of the dropwise addition of bromine, the reaction mixture is stirred for further 2 hours with the inside temperature being from −10° C. to −5° C. After stirring for further 1 hour at the inside temperature of 0° C., the reaction solution is measured by GC and, as a result, the area ratios of diamantane:monobromodiamantane : 4,9-dibromodiamantane:tribromodiamantane:other dibromodiamantanes are found to be 0:2.9:96.7:0.3:0. (A/(A+B+C+D+E)=0.96)

An aqueous solution of 4.3 g of sodium sulfite in 20 ml of pure water is added to the reaction solution. Subsequently, 120 ml of toluene and 180 ml of an aqueous solution of sodium sulfite are added thereto, followed by stirring at 50° C. and separating the solution. The organic layer is purified twice with each 100 ml of pure water. Subsequently, toluene is removed to concentrate under reduced pressure. 40 ml of acetone is added to the residue, followed by stirring for 30 minutes at 0° C. to crystallize. The thus-obtained crystals are filtered to obtain 14.7 g of 4,9-dibromodiamantane. Yield: 86%. Purity of the powder is found to be 99.0% by GC measurement of the powder.

EXAMPLES 4 to 10

Synthesis is conducted in the same manner as in Example 1 except for changing reaction conditions as shown in Table 1. GC measurement is conducted to determine isolation yield of 4,9-dibromodiamantane.

COMPARATIVE EXAMPLE 1

Reaction is conducted according to the process described in Journal of Organic Chemistry, 39, p.3000 (1974).

8.0 g of diamantane and 40 ml of bromine in a 100-ml flask are ice-cooled, and 0.40 g of aluminum bromide is added thereto over 2 hours, which is accompanied by generation of a seriously large amount of heat. Thereafter, the reaction solution is mixed for 3 hours with keeping the inside temperature at 0° C., and then 0.40 g of aluminum bromide is added thereto, followed by stirring for 2 hours at the inside temperature of 0° C. Here, measurement of the reaction solution by GC is conducted and, as a result, the area ratios of diamantane : monobromodiamantane:4,9-dibromodiamantane:tribromodiamantane:other dibromodiamantanes are found to be 0:5.0:46.0:6.0:43.0 (A/(A+B+C+D+E)=0.46).

Post-treatment according to the manner described in Example 1 provides 5.4 g of crude crystals. Measurement of the powder by GC reveals that the content of 4,9-dibromodiamantane is 85%. This crude product is purified by silica gel column chromatography (eluting solution:hexane/chloroform=98/2) and recrystallization from toluene/acetone to obtain 4.1 g of 4,9-dibromodiamantane. Purity of the product measured by GC is 95%.

COMPARATIVE EXAMPLES 2 to 5

Synthesis is conducted in the same manner as in Example 1 except for changing reaction conditions as shown in Table 1. GC measurement is conducted to determine isolation yield of 4,9-dibromodiamantane.

TABLE 1

|  | Lewis Acid (Aluminum Bromide) | Bromine ($Br_2$) | Reaction Solvent | A/(A + B + C + D + E) | Isolation Yield |
|---|---|---|---|---|---|
| Example 1 | 25.5 g (0.23 mol) | 128 ml (5.9 mol) | cyclohexane 340 ml | 0.96 | 70% |
| Example 4 | 17.0 g (0.15 mol) | 90 ml (4.1 mol) | cyclohexane 500 ml | 0.96 | 82% |
| Example 5 | 25.5 g (0.23 mol) | 75 ml (3.4 mol) | cyclohexane 340 ml | 0.88 | 65% |
| Example 6 | 25.5 g (0.23 mol) | 128 ml (5.9 mol) | cyclohexane 600 ml | 0.86 | 64% |
| Example 7 | 25.5 g (0.23 mol) | 128 ml (5.9 mol) | n-hexane 340 ml | 0.96 | 76% |
| Example 8 | 17.0 g (0.15 mol) | 128 ml (5.9 mol) | n-heptane 340 ml | 0.96 | 80% |
| Example 9 | 25.5 g (0.23 mol) | 128 ml (5.9 mol) | n-hexane 800 ml | 0.80 | 60% |
| Example 10 | 8.5 g (0.075 mol) | 220 ml (10 mol) | n-hexane 340 ml | 0.80 | 60% |
| Comparative Example 1 | 0.8 g (0.07 mol) | 40 ml (18 mol) | None | 0.46 | 27% |
| Comparative Example 2 | 25.5 g (0.23 mol) | 128 ml (5.9 mol) | dichloromethane 340 ml | 0.40 | 25% |
| Comparative Example 3 | 17.0 g (0.15 mol) | 90 ml (4.1 mol) | o-dichlorobenzene 340 ml | 0.45 | 30% |
| Comparative Example 4 | 17.0 g (0.15 mol) | 128 ml (5.9 mol) | carbon disulfide 340 ml | 0.25 | 10% |
| Comparative Example 5 | 8.5 g (0.075 mol) | 90 ml (4.1 mol) | dichloroethane 500 ml | 0.27 | 10% |

Numerals within the parentheses are mol numbers per mol of diamantane.

It can be seen that the synthesizing process of the invention is an excellent process which can provide 4,9-dibromodiamantane in high yield and in high isolation yield.

The entire disclosure of each and every foreign patent application from which the benefit of foreign priority has been claimed in the present application is incorporated herein by reference, as if fully set forth.

The invention claimed is:

1. A process for selectively producing 4,9-dibromodiamantane, comprising:
    a step of reacting diamantane with bromine in the presence of a Lewis acid and a solvent,
    wherein the solvent comprises a substituted or unsubstituted straight-chain saturated hydrocarbon containing from 3 to 10 carbon atoms, a substituted or unsubstituted branched-chain saturated hydrocarbon containing from 3 to 10 carbon atoms, or a substituted or unsubstituted cyclic saturated hydrocarbon containing from 3 to 10 carbon atoms, and
    a reaction solution after the step satisfies Formula (1):

$$A/(A+B+C+D+E) > 0.80 \quad \text{Formula (1)}$$

wherein A represents an area ratio (%) of 4,9-dibromodiamantane obtained by gas chromatography of the reaction solution, B represents an area ratio of diamantane, C represents a sum of an area ratio of 1-bromodiamantane and an area ratio of 4-bromodiamantane, D represents an area ratio of tribromodiamantane, and E represents a sum of an area ratio of 1,6-dibromodiamantane and an area ratio of 1,4-dibromodiamantane.

2. The process according to claim 1,
wherein the bromine ($Br_2$) is in an amount of from 3.5 to 7.0 mol per 1 mol of the diamantane.

3. The process according to claim 1,
wherein the solvent is selected from the group consisting of n-hexane, cyclohexane and n-heptane.

4. The process according to claim 1,
wherein the solvent is in an amount of from 3 to 7 ml per 1 g of the diamantane.

* * * * *